(12) United States Patent
Nakano et al.

(10) Patent No.: US 6,212,485 B1
(45) Date of Patent: Apr. 3, 2001

(54) METHOD OF ANALYSIS AND OPTIMAL DESIGN FOR A MICRO-INHOMOGENEOUS MATERIAL STRUCTURE BY A UNIFIED PROCEDURE OF MOLECULAR SIMULATION AND HOMOGENIZATION ANALYSIS

(75) Inventors: Masashi Nakano, Saitama-ken; Katsuyuki Kawamura, Tokyo; Yasuaki Ichikawa, Nagoya, all of (JP)

(73) Assignee: E.R.C. Co., Ltd., Nagoya (JP)

( * ) Notice: Subject to any disclaimer, the term of this patent is extended or adjusted under 35 U.S.C. 154(b) by 0 days.

(21) Appl. No.: 09/490,873

(22) Filed: Jan. 24, 2000

Related U.S. Application Data

(63) Continuation of application No. 09/001,519, filed on Dec. 31, 1997.

(30) Foreign Application Priority Data

Aug. 1, 1997 (JP) .................................................. 9-207596
Aug. 1, 1997 (JP) .................................................. 9-207596

(51) Int. Cl.$^7$ .................................................. G06G 7/48
(52) U.S. Cl. ........................................ 703/5; 703/6; 703/7
(58) Field of Search ........................................ 703/6, 5, 7

(56) References Cited

U.S. PATENT DOCUMENTS 5,260,882 * 11/1993 Blanco et al. ............................ 703/6
5,553,004 * 9/1996 Gronbech-Jensen et al. ......... 702/19

OTHER PUBLICATIONS

Schmitz et al.: "Description of RNA folding by Simulated Annealing", J. Mol. Biol.; vol. 255; pp. 254–266, 1996.*
Ogura et al.: "Molecular dynamics simulation of large deformation in an amorphous polymer"; Plymer; vol. 36; pp. 1375–1381.*

B.J. Alder and T.F. Wainwright (1957): "Phase Transition for a Hard Sphere System", *Journal of Chemical Physics*, vol. 27, pp. 1208–1209.

(List continued on next page.)

*Primary Examiner*—Kevin J. Teska
*Assistant Examiner*—Hugh Jones
(74) *Attorney, Agent, or Firm*—Lowe Hauptman Gilman & Berner, LLP

(57) ABSTRACT

A method for analyzing behavior of a structure made of a micro-inhomogeneous material, whose micro-structure includes plural constituent materials, and for optimally designing the micro-structure, uses a unified procedure of a molecular simulation method and a homogenization analysis. According to the method, the behavior of the micro-inhomogeneous material structure is analyzed and the micro-structure is optimally designed by (a) finding particle-data, such as positions, velocities and/or accelerations of all particles of atoms and/or molecules of the constituent materials of the micro-inhomogeneous material under given physicochemical conditions by using a molecular simulation method; (b) applying a statistical thermodynamics procedure to the particle-data for determining volume-averaged material properties, which are called bulk properties of constituent materials and of the interfaces of the micro-inhomogeneous material; (c) applying a homogenization analysis for a set of differential equations in which the bulk properties are used for predicting behavior of the structure, and calculating field variables distributed in the micro-inhomogeneous material; (d) comparing the field variables in each constituent material with a predetermined material standard of the field variables for judging whether or not the predetermined physicochemical conditions are feasible for the constituent materials; (e) if not, changing the predetermined physicochemical conditions, and applying the steps (a) to (d) repeatedly; (f) if the micro-inhomogeneous material is an artificial product, judging whether or not the micro-structure is appropriate in the sense that the field variables are allowable; and (g) if not, applying the steps (a) to (f) repeatedly after changing geometry and/or type of at least one of the constituent material(s).

16 Claims, 7 Drawing Sheets

OTHER PUBLICATIONS

T.J. Ahrens (1995): *Mineral Physics and Crystallography: A Handbook of Constants*, American Geophysical Union, pp. 49–54.

H.C. Andersen (1980): "Molecular Dynamic Simulations and Constant Pressure and/or Temperature", *Journal of Chemical Physics*, vo. 72, pp. 2384–2393.

N. Bakhvalov and G. Panasenko (1984): *Homogenization: Averaging Processes in Periodic Media*, Nauka Pub., Warsaw (English Translation, Kluwer Academic Pr., Dordrecht, 1989).

R. H. Boyd (1968): "Method for Calculation of the Conformation of Minimum Potential–Energy and Thermodynamic Functions of Molecules from Empirical Valence–Force Potentials—Application to the Cyclophanes", *Journal of Chemical Physics*, vol. 49, pp. 2575–2583.

Y. Ichikawa (1996): "Micro/Macro Properties of Materials: II. A Homogenization Theory for Visco–Elastic Material", *Suiyokai–Shi*, Kyoto University, vol. 22, No. 6, pp. 344–353 (in Japanese).

Y. Ichikawa, J.G. Wang, and G.C. Jeong (1996): "Micro/Macro Properties of Geomaterials: A Homogenization Method for Viscoelastic Problem", *International Journal of Structural Engineering and Mechanics*, vol. 4, No. 6, pp. 631–644.

K. Kawamura (1990): *Molecular Simulation Using Personal Computer*, Kaibundo (in Japanese).

K. Kawamura (1992): "Interatomic potential models for molecular dynamics simulations of multi–component oxides", in *Molecular Dynamics Simulations* (ed. F. Yonezawa), Springer, pp. 88–97.

G. Marom (1989): "Environmental Effect on Fracture Mechanical Properties of Polymer Composites", in *Application of Fracture Mechanics to Composite Materials*, ed. K. Friedrich, Elsevier.

N. Kumagai, K. Kumamura and T. Yokokawa (1994): "An interatomic potential model for H2O: applications to water and ice polymorphs", *Molecular Simulation*, vol. 12(3–6), pp. 177–186.

N. Metropolis, A. W. Rosenbluth, M.N. Rosenbluth, A. H. Teller, and E. Teller, (1953).

"Equation of state calculation by fast computing machines", *Journal of Chemical Physics*, vol. 21, pp. 1087–1092.

S. Nose and M. L. Klein (1983): "Constant Pressure Dynamics for Molecular Systems", *Molecular Physics*, vol. 50, pp. 255–268.

K. Okada and E. Osawa (1989): "Outline of Molecular Simulation", *Introduction of Molecular Simulation* (ed. by K. Okada and E. Osawa), Chap. 1, Kaibundo, pp. 1–8 (in japanese).

A. Rahman (1964): "Correlations in the Motion of Atoms in Liquid Argon", *Physical Review*, vol. 136, pp. A405–A411.

F.H. Stillinger and A. Rahman (1972): "Molecular Dynamics Study of Temperature Effects on Water Structure and Kinetics", *Journal of Chemical Physics*, vol. 57, pp. 1281–1292.

E. Sanchez–Palencia (1980): *Non–Homogeneous Media and Vibration Theory*, Lecture Notes in Physics, 127, Springer–Verlag.

K. B. Wiberg (1965): "A Scheme for Strain Energy Minimization Application to the Cycloalkanes", *Journal of American Chemical Society*, vol. 87, pp. 1070–1078.

* cited by examiner

Figure 1. Micro-inhomogeneous material and the concept of three phases of the material profile, that is, the macro-continuum level, the micro-continuum level with micro-inhomogeneity and the molecular level.
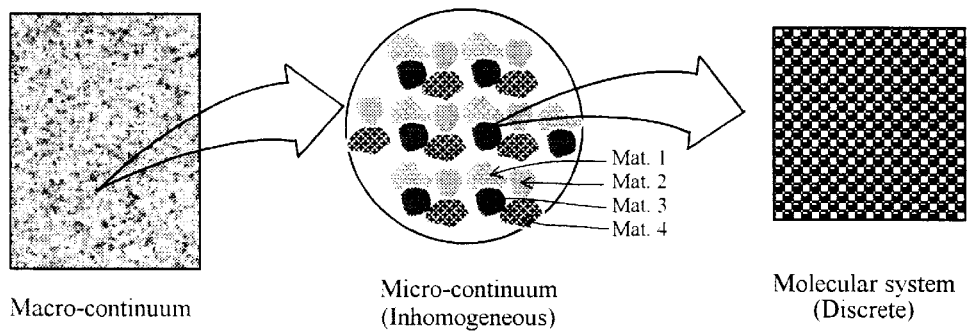
Figure 2. A schematic diagram of the unified method of MS and HA for analyzing and designing the micro-inhomogeneous material structure optimally.
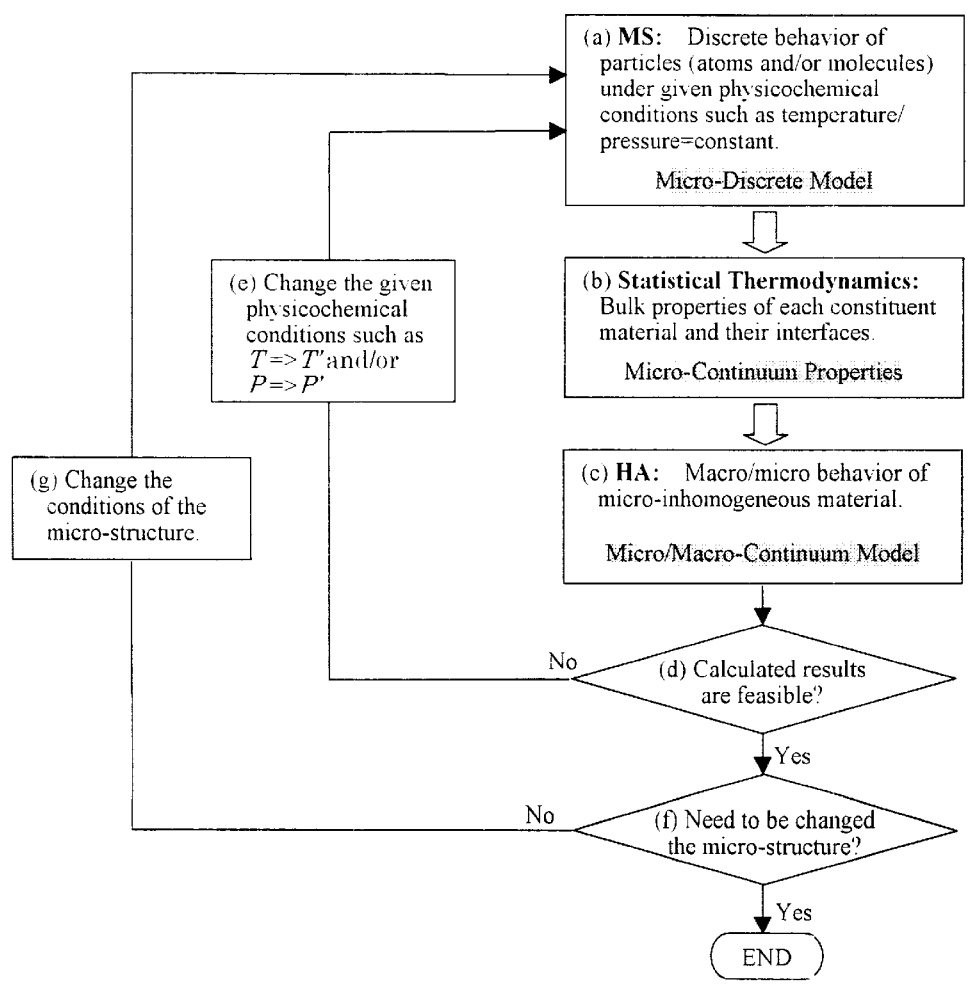

Figure 3. Schematic diagram of MD and the subsequent statistical thermodynamic procedure.
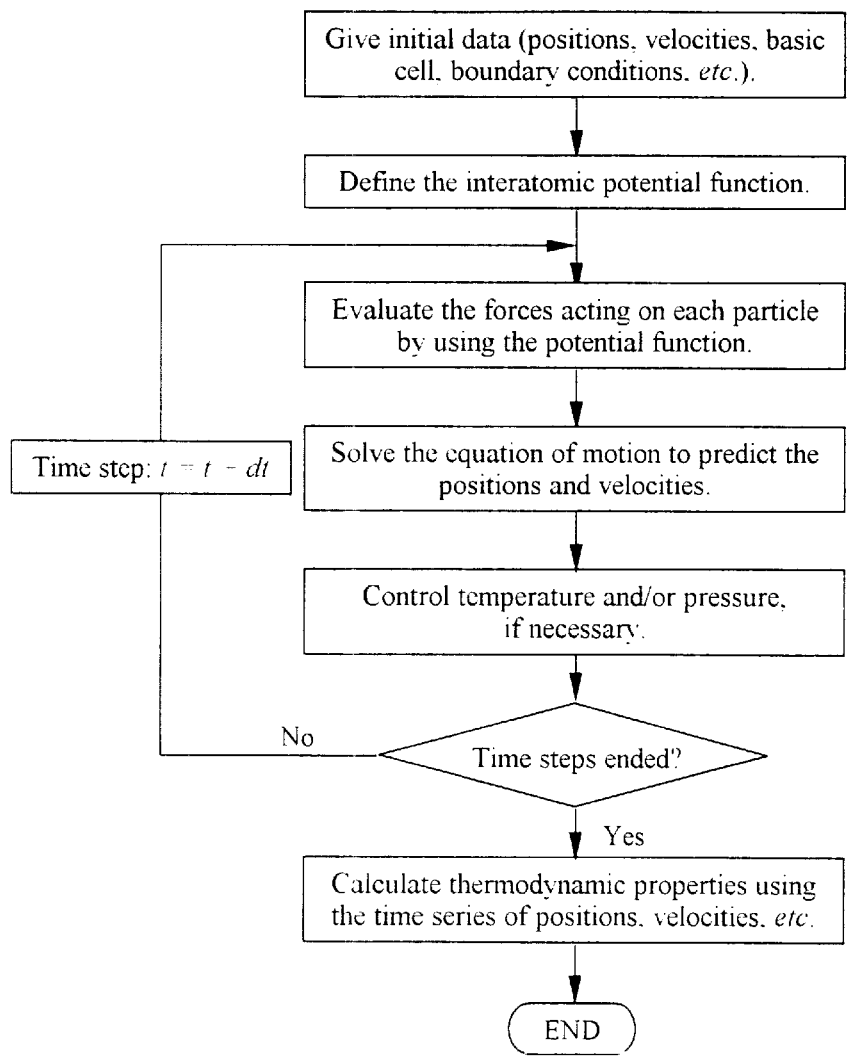

Figure 4. Macroscale and microscale problems in HA.
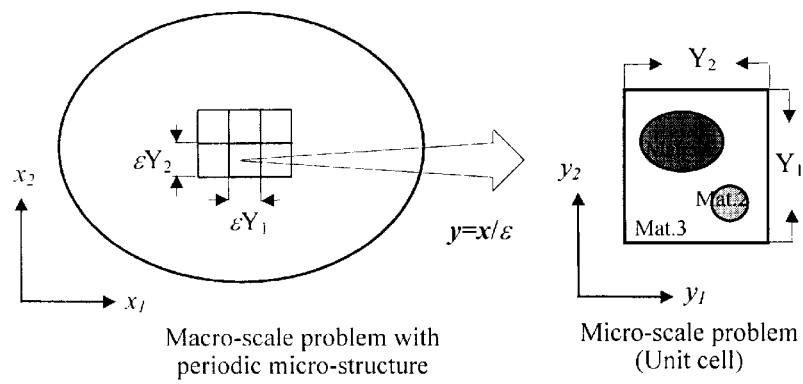
Macro-scale problem with periodic micro-structure
Micro-scale problem (Unit cell)
Figure 5. The example specimen of granite for analyzing it by the method of the invention.
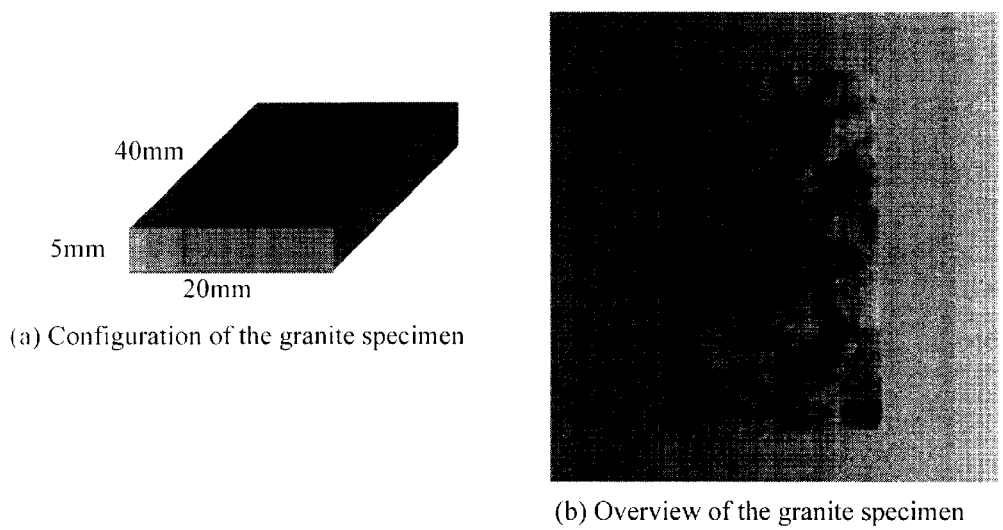
(a) Configuration of the granite specimen
(b) Overview of the granite specimen
PRIOR ART

Figure 6  MD model parameters of granite minerals (quartz, feldspar and mica).

(a) MD parameters for quartz

| | atomic mass $w$ | ionic charge $z$ | $a$ [A] | $B$ [A] | $c$ [kcal$^{1/2}$A$^3$ mole$^{-1/2}$] | Morse term | $D$ [kcal/mole] | $\beta$ [1/A] | $r^*$ [A] |
|---|---|---|---|---|---|---|---|---|---|
| O | 16.00 | -1.200 | 1.926 | 0.160 | 20.000 | | | | |
| Si | 28.09 | 2.400 | 0.945 | 0.090 | 0.000 | Si-O | 74.0 | 2.00 | 1.51 |

(b) MD parameters for albite (a kind of feldspar)

| | atomic mass $w$ | ionic charge $z$ | $a$ [A] | $b$ [A] | $c$ [kcal$^{1/2}$A$^3$ mole$^{-1/2}$] | Morse term | $D$ [kcal/mole] | $\beta$ [1/A] | $r^*$ [A] |
|---|---|---|---|---|---|---|---|---|---|
| O | 16.00 | -1.2886 | 1.926 | 0.160 | 20.000 | | | | |
| Si | 28.09 | 2.400 | 0.945 | 0.090 | 0.000 | Si-O | 74.0 | 2.00 | 1.51 |
| Al | 26.98 | 2.109 | 1.066 | 0.090 | 0.000 | Al-O | 40.0 | 2.00 | 1.64 |
| Na | 22.99 | 1.000 | 1.260 | 0.080 | 10.000 | | | | |

(c) MD parameters for muscovite (a kind of mica)

| | atomic mass $w$ | ionic charge $z$ | $a$ [A] | $b$ [A] | $c$ [kcal$^{1/2}$A$^3$ mole$^{-1/2}$] | Morse term | $D$ [kcal/mole] | $\beta$ [1/A] | $r^*$ [A] |
|---|---|---|---|---|---|---|---|---|---|
| O | 16.00 | -1.3025 | 1.907 | 0.150 | 22.000 | | | | |
| Si | 28.09 | 2.400 | 0.890 | 0.080 | 0.000 | Si-O | 74.0 | 2.00 | 1.51 |
| Al | 26.98 | 2.250 | 0.957 | 0.080 | 0.000 | Al-O | 35.0 | 2.00 | 1.66 |
| K | 39.10 | 1.000 | 1.573 | 0.120 | 16.000 | | | | |
| H | 1.01 | 0.340 | 0.053 | 0.044 | 0.000 | H-O | 75.0 | 2.76 | 0.82 |

Figure 7. The stress $\sigma_1$ ($x$-axial stress) versus strains for each direction ($\varepsilon_1$ to $\varepsilon_3$ are axial strains, and $\varepsilon_4$ to $\varepsilon_6$ are shear strains) for quartz calculated by the constant-(NPT) ensemble MD and the subsequent statistical thermodynamics procedure.
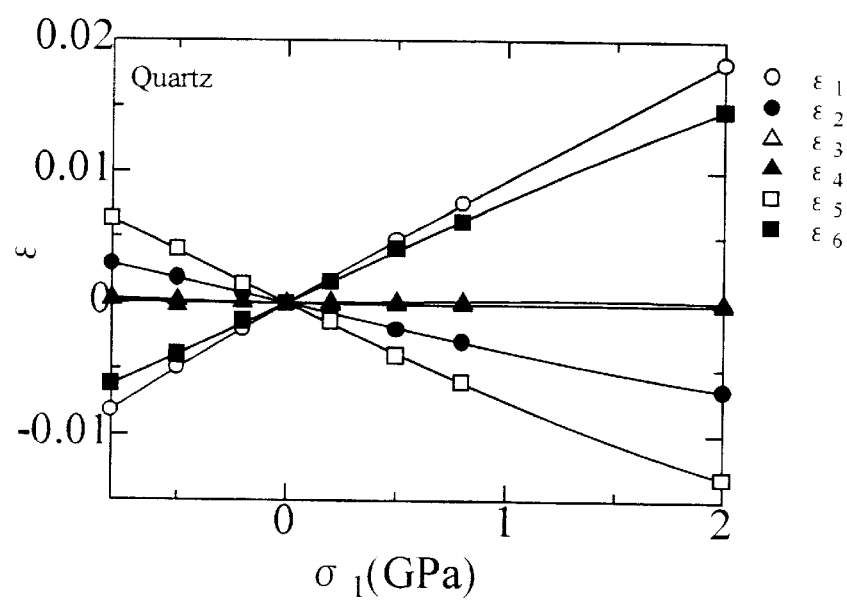

Figure 8. Model of granite for HA.
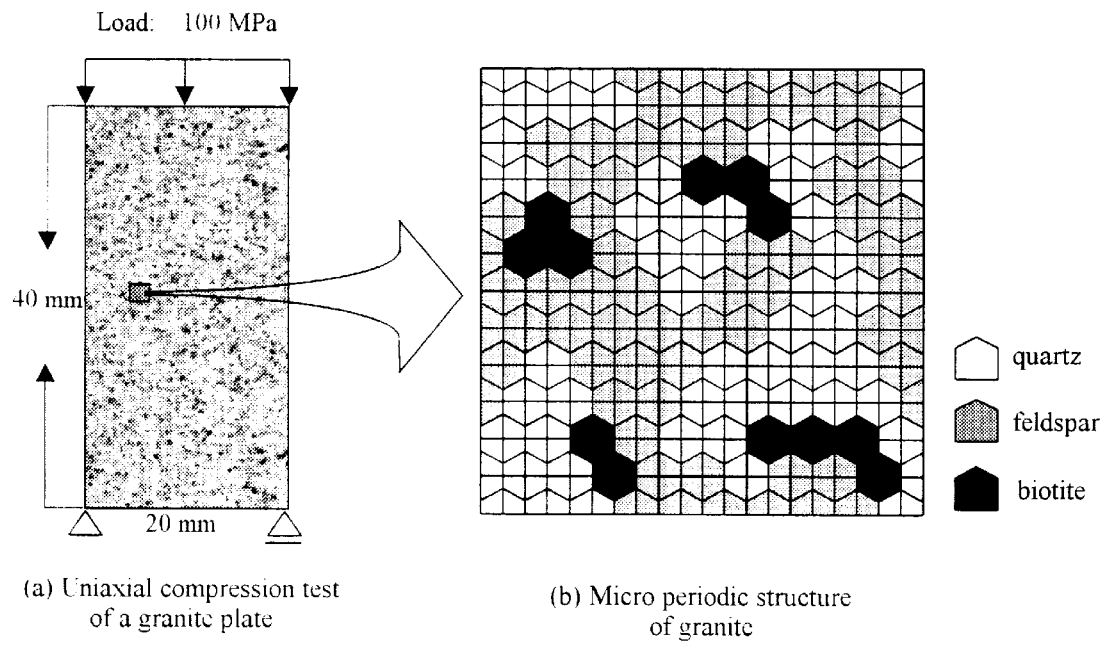
(a) Uniaxial compression test of a granite plate
(b) Micro periodic structure of granite
Figure 9. The microscale stress distribution of the granite model.
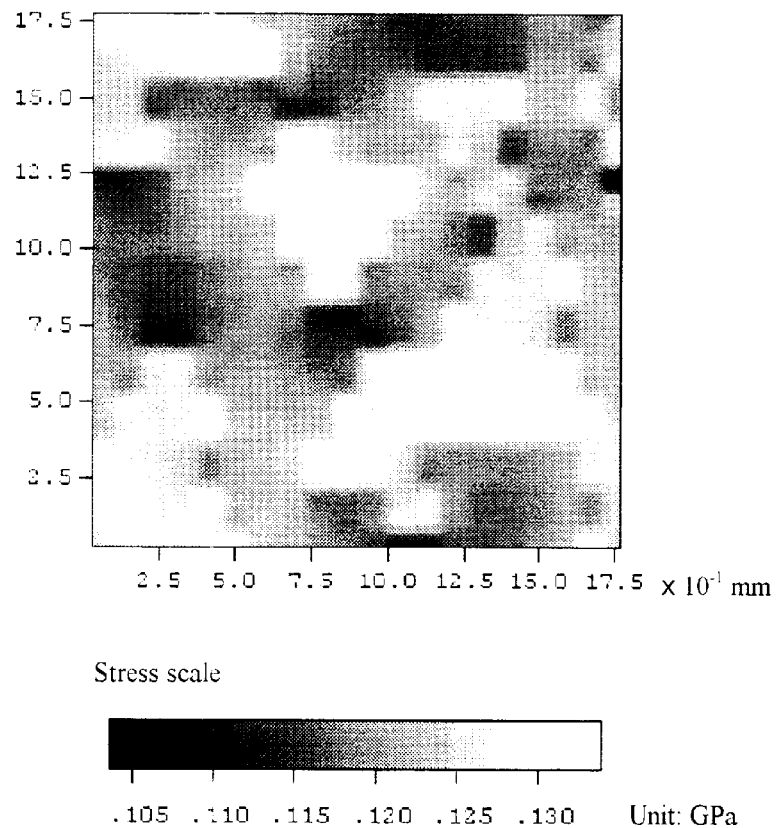
Stress scale
Unit: GPa Figure 10. An example of composite material; polished cross section of glass-fiber woven fabric/epoxy composites (Marom 1989).
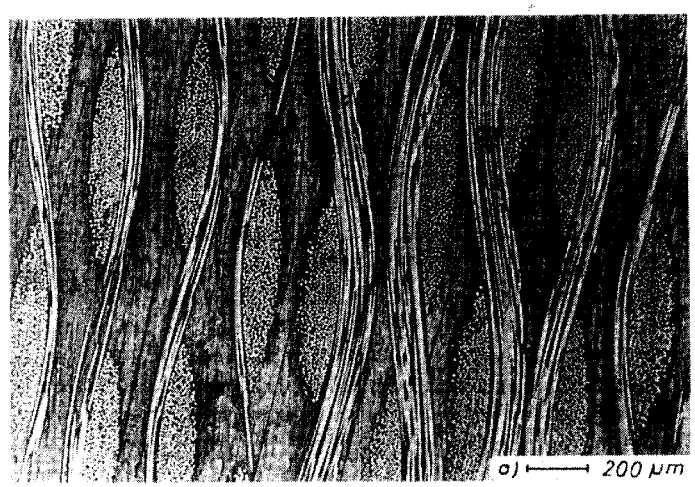
PRIOR ART
Figure 11. An example of the structure using composite materials; Space Shuttle.
PRIOR ART
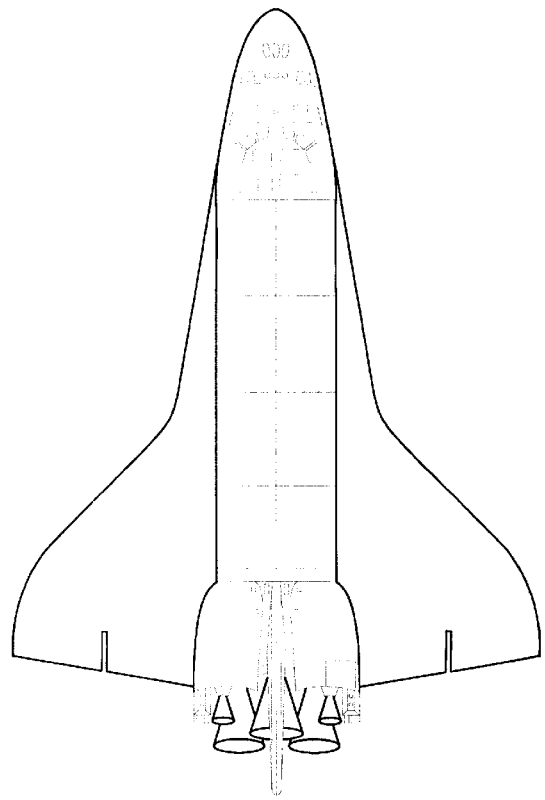

METHOD OF ANALYSIS AND OPTIMAL DESIGN FOR A MICRO-INHOMOGENEOUS MATERIAL STRUCTURE BY A UNIFIED PROCEDURE OF MOLECULAR SIMULATION AND HOMOGENIZATION ANALYSIS

This application is a Continuation of application Ser. No. 09/001,519, filed Dec. 31, 1997.

FIELD OF THE INVENTION

This invention relates to a method of analysis and optimal design for a structure made of a micro-inhomogeneous material, such as composite material, ceramics, concrete, geological material (such as rock and soil) and polycrystalline material including metal, by using a unified procedure of a molecular simulation method (hereafter abbreviated as MS) and a homogenization analysis (hereafter abbreviated as HA).

BACKGROUND OF THE INVENTION

When analyzing the behavior of an engineering structure made of complex mixed materials, a three phase concept of the material profile can be introduced. The first phase of the profile is at a macro-continuum level of the structure. That is, the structure is built as an assembly of macro-continuum elements. The second phase is at a micro-continuum level of the structure. It should be noted that most macro-continuum materials, which seem to be homogeneous in the macro-continuum level, in fact comprise several constituent components when considered from the microscopic point of view. This kind of material is said to be micro-inhomogeneous. The third phase of the profile is at a molecular level. This phase is founded on the physical fact that each constituent material of the micro-continuum consists of a vast number of atoms and/or molecules.

As an example, a bridge is considered as a target structure that is made of granite. The granite is a macro-continuum material. Granite includes three major component minerals such as quartz, feldspar and mica in the micro-continuum level thereof. That is, the micro-structure of granite comprises three constituent minerals, each in turn including a set of atoms/molecules that constitutes a molecular system. Similarly, a concrete dam structure has the same phases. That is, the concrete is a macro-continuum material; gravel, sand and cement paste are micro-continuum materials; and each of the micro-continuum materials constitutes a molecular system.

When designing an engineering structure with plural member elements, it is known to follow a theory of macro-phenomenological mechanics, and to perform a series of experiments in order to determine the macro-mechanical properties of each macro-continuum element. It should be recalled that the material properties obtained in these experiments are averaged in the specimen. This procedure is applied in the same manner in many fields of mechanics such as mechanical engineering and civil engineering.

In order to overcome the theoretical insufficiency involved in the above described macro-phenomenological theory, it is commonly believed that for the micro-inhomogeneous material the size of experimental specimens must be more than ten times larger than the largest size of the constituent components. However, in fact it is not truly known if this belief is true. Furthermore, it is difficult for the macro-phenomenological theory to recognize what happens in the micro-continuum level, although the local phenomena are directly related to the global behavior of the structure.

It can thus be said that the conventional macro-phenomenological procedure is not appropriate for analyzing the behavior of the micro-inhomogeneous material, especially where such a material is used under very extreme engineering condition such as high pressure, high temperature and/or long elapsed time.

In analyzing the behavior of micro-inhomogeneous material two essential problems must be solved. Firstly, it is necessary to determine characteristics of constituent components of the micro-continuum which are directly affected by their molecular movement. Secondly, there must be developed an approach to relating the microscale characteristics to the macroscale behavior of the structure and the macro-continuum elements thereof.

The prior art has not yet succeeded in developing such a fully unified procedure to analyze the molecular movements of the constituent components of the micro-continuum with respect to the macroscale behavior of the structure, much less to design the micro-structure optimally based on such considerations.

MS is a known type of a computer simulation technique. In an MS computation, one gives a material system which consists of particles, atoms and/or molecules, and provides two physical laws, that is, the interatomic interaction potential and the equation of motion or equilibrium. Positions, velocities and/or accelerations of all particles are then calculated under the foregoing physical laws. A statistical thermodynamics procedure is applied to the simulated results, and one can estimate bulk-based physicochemical properties of the material (hereinafter called the bulk properties of the material) such as structure factor of the solid crystal. It is noted that the bulk properties represent thermodynamical averages of the ensemble of particles.

Three classes of MS methods are known:

1) the Monte Carlo method (hereafter abbreviated as MC), 2) the Molecular Mechanics method (hereafter abbreviated as MM), and 3) the Molecular Dynamics method (hereafter abbreviated as MD).

MC, developed by Metropolis et al, estimates the statistical equilibrium state of particles by generating their displacements randomly. Various thermomechanical properties are then calculated by averaging over the states in the Markov chain.

MM is applied for a molecular system which consists of a finite number of atoms, and determines the equilibrium state by optimizing the structure and potential energy. The bulk properties are calculated by using statistical thermodynamics procedure. MM is mainly used in the field of organic chemistry.

On the other hand, MD solves the equation of motion for a system of particles under a given interatomic interaction potential by using a time-discrete finite difference scheme, and the whole time trajectories of particles are specified. The bulk properties are calculated by using statistical thermodynamics procedure for the results.

As MC and MM provide no knowledge of chronological trajectories of particles, these techniques are incapable of considering quantities that are defined in terms of particle motion, such as diffusion. In this sense, except for computational efficiency, MD is more useful so the MD procedure is shown herein as a typical example of MS.

In the MD calculation, the law of conservation of linear momentum is applied for every particle to get the following equation of motion for the i-th component:

$$m_i \frac{dv_i}{dt} = F_i \qquad (1)$$

where $m_i$ is the mass of the i-th particle, $v_i = dr_i/dt$ is its velocity at the position $r_i$, and the force $F_i$ is calculated from the potential function $U_{ij}$ between two particles by $$F_i = \sum_{j(i \neq j)} F_{ij}; \qquad (2)$$

$$F_{ij} = -\nabla U_{ij}.$$

The MD system usually contains many particles of atoms and/or molecules in a basic cell, and (for simplicity of calculation) the method uses a three dimensional periodic lattice, which is repeated in each direction. Under these conditions one solves a time discrete form of the equation of motion, and the instantaneous position, velocity and acceleration of each particle are specified. Then, using these results and statistical thermodynamic theory, one computes for the material the bulk properties and their change with time, such as density, diffusivity of atoms, molecular vibrations, temperature- and/or pressure-dependent nonlinear elastic moduli, viscosity, heat capacity and heat conductivity.

The interatomic potential function for all atom-atom pairs plays an essential role for the MD calculation. Equation (3) presents a potential function developed by Kawamura so as to reproduce structural and physical properties of several oxide crystals such as quartz, corundum and feldspars properly.

2-body term:

$$U_{ij}(r_{ij}) = \frac{z_i z_j e^2}{4\pi\varepsilon_0 r_{ij}} + f_0(b_i + b_j)\exp\left[\frac{a_i + a_j - r_{ij}}{b_i + b_j}\right] - \frac{c_i c_j}{r_{ij}^6} + D_{ij}[\exp\{-2\beta_{ij}(r_{ij} - r_{ij}^*)\} - 2\exp\{-\beta_{ij}(r_{ij} - r_{ij}^*)\}]. \qquad (3)$$

The right hand side of this equation shows the Coulomb, the short-range repulsion, the van der Waals and the Morse terms, respectively. These terms are selectively used for some materials due to the nature of the interaction. For water a 3-body term is also added to the H—O—H interaction because of its $Sp^3$ hybrid orbital.

3-body term:

$$U_{ijk}(\theta_{ijk}, r_{ji}, r_{jk}) = f_k[1 - \cos\{2(\theta_{ijk} - \theta_0)\}](k_i k_j)^{1/2}, \qquad (4)$$

$$k_i = \frac{1}{\exp\{g_r(r_{ji} - r_m)\} + 1}.$$

Parameters $\{z, a, b, c\}$ and $\{D, \beta, r^*\}$ for the 2-body term, and $\{f_k, \theta_0, g_r, r_m\}$ for the 3-body term are specified by using experimental data of structural and physical properties of relevant materials.

Many types of simulation schemes have been developed in MD. For example, in the early stage of MD there was employed a scheme where the number of particles N, the volume V and the total energy E are constant (the constant-(NVE) ensemble), while in the 1980's there was developed a scheme in which the number of particles N, the pressure P and the temperature T are constant (the constant-(NPT) ensemble). MD generates information at the molecular level such as position, velocity and acceleration of each particle.

Statistical thermodynamics provide averaged quantities of the system which are called the bulk properties. For example, one can calculate the temperature as $$T = \frac{2}{3k_B}\langle\varepsilon_k\rangle \qquad (5)$$

where $k_B$ is Boltzmann's constant, and $$\varepsilon_k = \frac{1}{2}m_k v_k \cdot v_k \qquad (6)$$

is the kinetic energy of the k-th particle with its mass $m_k$ and velocity $v_k$. Note that $\langle A \rangle$ gives the time average of a quantity $A(t)$ taken over a long time interval:

$$\langle A \rangle = \lim_{T \to \infty} \frac{1}{T}\int_0^T A(t)dt = \frac{1}{N_s N}\sum_{n=0}^{N_s - 1}\sum_{k=1}^{N} A_k(t_0 + n\Delta\tau). \qquad (7)$$

The right hand side term is used for a discrete system with N-particles for $N_s$-number of a time slice $\Delta\tau$. Then, by applying the virial theorem the pressure P is calculated as $$P = \frac{Nk_B T}{V} + \frac{1}{3V}\left\langle\sum_i r_i \cdot F_i\right\rangle \qquad (8)$$

where $r_i$ is the position vector and $F_i$ the force acting on the i-th particle. Similar to this, one can calculate the stress tensor which is the force per unit area acting on three coordinate surfaces in the three dimensional case. On the other hand, if one uses the constant-(NPT) ensemble scheme for example, the normal strain $\epsilon_{xx}$ in the x-direction is calculated by $$\varepsilon_{xx} = \frac{L_x^c}{L_x} \qquad (9)$$

where $L_x$ is the original size of the basic cell in the x-direction, and $L_x^c$ is its size after relaxation by the MD calculation. Other components of strains including shear components can be calculated in a similar manner. If the pressure is changed, one gets a different value of strain. Plotting these values yields a stress-strain relation in the micro-continuum level. Thus, one gets a stress or strain dependent type of the Young's modulus E.

Though MD is quite powerful for simulating the true behavior of materials, it is impossible to use this method directly for designing an engineering structure on a human size scale, such as a car, an airplane and a bridge, because such structures involve extremely large numbers of molecules. Note that one mole of material (equivalent to 12 g of carbon) consists of $6.0221367 \times 10^{23}$ molecules, and even if the fastest computer known at present were used, one can calculate a system with at most $10^6$ molecules. It is thus impossible to use MS in a simple manner for designing a practical engineering structure. This circumstance will not be changed in near future.

The HA method, which is based on a new type of perturbation theory, has been developed for micro-inhomogeneous media with a periodic microstructure. This method allows a determination of both macroscopic and microscopic distribution of field variables such as temperature, displacement, stress and strain. It is noted that the perturbation theory is a method mainly for solving nonlinear problems.

The simplest example of HA is shown herein for applying the one dimensional static equilibrium problem, which is described by the following equation.

$$\frac{d}{dx}\left(E\frac{du^\varepsilon(x)}{dx}\right) = f, \tag{10}$$

where $u^\varepsilon(x)$ denotes the displacement which changes rapidly in the micro-continuum level, E Young's modulus, and f the body force. Note that E also varies in that micro-continuum level. Let the size of the microstructure be $\varepsilon Y$, and one introduces a local coordinate system y in the micro-continuum level. The global coordinate x is related to the local one y by $$y = \frac{x}{\varepsilon}. \tag{11}$$

By using this $\varepsilon$, a perturbation expansion is introduced by $$u^\varepsilon(x) \cong u_0(x,y) + \varepsilon u_1(x,y) + \varepsilon^2 u_2(x,y) + \Lambda \tag{12}$$

where $u_0(x,y)$, $u_1(x,y)$, $u_2(x,y)$, ... are periodic functions satisfying the condition $u_i(x,y+Y) = u_i(x,y)$ (i=0,1,2, . . .). If the two coordinates x and y are used, the differentiation is changed as $$\frac{d}{dx} \Rightarrow \frac{\partial}{\partial x} + \frac{1}{\varepsilon}\frac{\partial}{\partial y}. \tag{13}$$

On substituting the perturbed expansion (12) and the differentiation form (13) into the equilibrium equation (10), and setting each term of the series for $\varepsilon$ to be zero, the following relations can be obtained:

$$\varepsilon^{-2} - \text{term: } \frac{\partial}{\partial y}\left(E\frac{\partial u_0}{\partial y}\right) = 0. \tag{14}$$

This implies that $u_0$ is the function of only the global coordinate x, that is, $u_0 = u_0(x)$.

$$\varepsilon^{-1} - \text{term: } \frac{\partial}{\partial y}\left(E\frac{\partial u_1}{\partial y}\right) = -\frac{\partial}{\partial y}\left(E\frac{\partial u_0}{\partial x}\right). \tag{15}$$

This gives a differential equation to determine $u_1(x,y)$ in y, and on introducing a separation of variable $$u_1(x, y) = N(y)\frac{\partial u_0}{\partial x} \tag{16}$$

yields a differential equation for the characteristic function N(y):

$$\frac{d}{dy}\left\{E(y)\frac{d}{dy}(N(y)+y)\right\} = 0. \tag{17}$$

This equation is called the microscale equation.

$$\varepsilon^0 - \text{term: } \frac{\partial}{\partial y}E\frac{\partial u_2}{\partial y} = f(x, y) - \frac{\partial}{\partial x}E\frac{\partial u_0}{\partial x} - \frac{\partial}{\partial y}E\frac{\partial u_1}{\partial x} - \frac{\partial}{\partial x}E\frac{\partial u_1}{\partial y} \tag{18}$$

For this equation, the following average operation is introduced:

$$\langle \cdot \rangle = \frac{1}{|Y|}\int_0^Y \cdot\, dy, \tag{19}$$

then the macroscale equation is obtained for determining $u_0$ as $$\frac{d}{dx}\left(E^*\frac{du_0}{dx}\right) = f^* \tag{20}$$

where $$E^* = \left\langle E(y) + E(y)\frac{dN}{dy}\right\rangle, f^* = \langle f(x, y)\rangle. \tag{21}$$

The quantity $E^*$ is called the homogenized elastic coefficient. Thus, first the microscale equation is solved under the periodic boundary condition to get the characteristic function N(y). One substitutes it for the definition of the homogenized elastic coefficient, and solving the macroscale equation which is of the same form of the original equation of equilibrium yields $u_0$. Now one gets $u_1$ by using $u_0$ and N(y), then $u_2$ can be calculated by the differential equation of $\varepsilon^0$-term. However since the value of terms $\varepsilon^k u_k(x,y)(k \geq 2)$ is thought to be small, one sets $$u^\varepsilon(x) \cong u_0(x,y) + \varepsilon u_1(x,y). \tag{22}$$

In this case, the strain can be obtained as $$e^\varepsilon = \frac{du^\varepsilon(x)}{dx} = \frac{\partial u_0}{\partial x} + \frac{\partial u_1}{\partial y} + \varepsilon\frac{\partial u_1}{\partial x} \tag{23}$$

and the stress is given by $$\sigma^\varepsilon = Ee^\varepsilon. \tag{24}$$

In practical engineering problems with two or three dimensions, a finite element approximation method is applied for solving the above mentioned microscale and macroscale equations.

The various methods of MS and HA have been developed in different fields, and no intercorrelation has been tried in these two fields. Both the MS methods and HA involve difficulties in attempting to apply them to simulate the behavior of a practical engineering structure made of a micro-inhomogeneous material: MS methods can only treat a system with far less particles than in a practical structure, while in HA it is difficult to find bulk properties of each constituent material and their interfaces. In view of the difficulties of the prior art, it is thus important to establish an accurate method for analyzing the behavior of a structure made of micro-inhomogeneous material and for designing the micro-structure of the micro-inhomogeneous material optimally in the case of manufacturing.

It is accordingly an object of the invention to overcome the difficulties of the prior art and to provide a novel method for analyzing and designing a structure made of micro-inhomogeneous material.

SUMMARY OF THE INVENTION

The present invention overcomes the difficulties of the prior art, by providing a unified MS and HA procedure for analyzing the behavior of a micro-inhomogeneous material and for designing the micro-structure of the micro-inhomogeneous material optimally in the case of manufacturing. In accordance with the inventive method, it is possible to calculate an accurate behavior of the micro-inhomogeneous material in a seamless manner starting from the molecular level to the macro-continuum level, and to design its micro-structure optimally. Because the invention makes possible an accurate prediction of the behavior of micro-inhomogeneous materials which are used under extreme conditions such as high temperature and/or high pressure, and because the optimal arrangement of the micro-structure is made possible, the invention thus makes it possible to design properly a practical structure made of micro-inhomogeneous materials. That is, even if the structure is used under ultimate conditions, the invention makes it possible to predict the behavior accurately and to show an effective way to maintain such structures safely.

Thus the invention provides an innovative method for analyzing a structure made of micro-inhomogeneous materials, such as composite material, ceramics, concrete, geological material (rock and soil) and polycrystalline material, and for designing the micro-structure optimally. The inventive method may include the following procedures: (a) By applying MS, positions $r_i$, velocities $v_i$ and/or accelerations ai of all particles are determined for a system of particles of atoms and/or molecules that consists of constituent materials of the micro-inhomogeneous material under given physicochemical conditions such that temperature T and pressure P are constant. Symbolically the results of MS are here called a particle-data. (b) By applying the statistical thermodynamics procedure for the particle-data, physicochemical properties such as the Young's modulus E, the thermal conductivity k and the surface-to-surface spring constant of the constituent materials and their interfaces, comprising boundaries of plural constituent materials, are determined. The specified properties (called the bulk properties) are functions of the given physicochemical conditions. Thus, these properties are functions of the particle-data. For example, the Young's modulus E is usually dependent on temperature T and/or pressure P, and thus depends on the particle-data (that is, $E(T(r_i, v_i, a_i), P(r_i, v_i, a_i))=E(r_i, v_i, a_i)$). (c) By applying HA for a set of differential equations in which the bulk properties obtained by the above mentioned statistical thermodynamics procedure are used, the behavior of the structure is predicted to calculate field variables such as stress, strain, temperature and water flow distributed in the macro-continuum and micro-continuum materials. (d) By comparing the calculated field variables in each micro-continuum material and interfaces with a predetermined material standard such as a failure criterion, it is judged whether the given physicochemical conditions are feasible for each constituent material. (e) If not, the steps (a) to (d) are repeatedly applied after changing the given physicochemical conditions, for example, the temperature and pressure such as T=>T' and P=>P'. (f) If the targeted micro-inhomogeneous material is an artificial product such as composite material and ceramic, it is judged whether the micro-structure is appropriate in the sense that the field variables such as stress are allowable. (g) If not, the steps (a) to (f) are repeatedly applied after changing the geometry and/or type of at least one of the constituent material(s). Then, the micro-structure can be optimally arranged. These and other objects, features and advantages of the present invention will become readily apparent to those skilled in the art from the following description and drawings, wherein there is shown and described a preferred embodiment of the invention, simply by way of illustration and not of limitation of one of the best modes (and alternative embodiments) suited to carry out the invention. The invention itself is set forth in the claims appended hereto. As will be realized upon examination of the specification and drawings and from practice of the same, the present invention is capable of still other, different, embodiments and its several details are capable of modifications in various obvious aspects, all without departing from the scope of the invention as recited in the claims. Accordingly, the drawings and the descriptions provided herein are to be regarded as illustrative in nature and not as restrictive of the invention.

BRIEF DESCRIPTION OF THE DRAWINGS

The accompanying drawings, incorporated into and forming a part of the specification, illustrate several aspects of a preferred embodiment of the present invention and, together with the description, serve to explain the principles of the invention. In the drawings:

FIG. 1 shows a typical micro-inhomogeneous material and illustrates three phases of the material profiles, including the macro-continuum level, the micro-continuum level with micro-inhomogeneity and the molecular level;

FIG. 2 provides a schematic illustration of the present invention, showing a unified method of MS and HA for optimally analyzing and designing the micro-inhomogeneous material structure;

FIG. 3 is a schematic illustration of MD and the subsequent statistical thermodynamics procedure;

FIG. 4 is an illustration defining macroscale and microscale problems in HA;

FIG. 5 shows a specimen of prior art granite for analysis by the method of the invention;

FIG. 6 is a table showing MD model parameters of granite minerals (quartz, feldspar and mica);

FIG. 7 shows the stress-strain relation of quartz calculated by the constant-(NPT) ensemble MD and the subsequent statistical thermodynamics procedure;

FIG. 8 shows a model of granite for HA;

FIG. 9 shows the microscale stress distribution of the granite model;

FIG. 10 shows an example of a prior art composite material, polished cross section of glass-fiber en fabric/epoxy composites; and FIG. 11 shows an example of a structure using composite materials in the form of a prior art Space Shuttle.

DETAILED DESCRIPTION OF THE INVENTION

The invention will now be described in detail with reference to the drawings. Shown in FIG. 1 is a micro-inhomogeneous material as treated in accordance with the present invention. This material involves three phases of the profiles, that is, the macro-continuum level, the micro-continuum level with micro-inhomogeneity and the molecular level. It should be noted that constituent components of the micro-continuum shown in FIG. 1 are Mat. 1, 2, 3 and 4, which gives the micro-structure.

FIG. 2 shows the schematic diagram of the present invention, that is, the unified method of MS and HA which includes the following procedures: (a) Calculation starts by using MS. Thus, for a system of particles of atoms and/or molecules that consists of constituent materials of the micro-inhomogeneous material, the positions $r_i$, velocities vi and/or accelerations $a_i$ of all particles are determined under given physicochemical conditions such that temperature T and pressure P are constant. Symbolically the results of MS are called particle-data. (b) The statistical thermodynamics procedure for the particle-data is applied to determine physicochemical properties such as Young's modulus E, the thermal conductivity k and the surface-to-surface spring constant of the constituent materials and their interfaces that consist of boundaries of plural constituent materials. The specified properties (called the bulk properties) are functions of the given physicochemical conditions, and are thus functions of the particle-data. For example, the Young's modulus E is usually dependent on temperature T and/or pressure P, and thus depends on the particle-data (that is, $E(T(r_i, v_i, a_i), P(r_i, v_i, a_i))=E(r_i, v_i, a_i)$). (c) By applying HA for a set of differential equations in which the bulk properties obtained by the above mentioned statistical thermodynamics procedure are used, the behavior of the structure is predicted to calculate field variables such as stress, strain, temperature and water flow distributed in the macro-continuum and micro-continuum materials. (d) By comparing the calculated field variables in each micro-continuum material and interfaces with a predetermined material standard such as a failure criterion, it is judged whether the given physicochemical conditions are feasible for each constituent material. (e) If not, the steps (a) to (d) are repeatedly applied after changing the given physicochemical conditions, for example, the temperature and pressure such as T=>T' and P=>P'. (f) If the targeted micro-inhomogeneous material is an artificial product such as composite material and ceramic, it is judged whether the micro-structure is appropriate in the sense that the field variables such as stress are allowable. (g) If not, the steps (a) to (f) are repeatedly applied after changing the geometry and/or type at least one of the constituent material(s). Then, the micro-structure can be optimally arranged.

In the following description MD is employed as a typical exemplary method of MS. It should be recognized, however, that any other method of MS (whether or not as hereinabove described) may be used. Thus, FIG. 3 shows the schematic diagram of MD and the subsequent statistical thermodynamics procedure. Details of MD are presented in the preceding section BACKGROUND OF THE INVENTION.

Macroscale and microscale problems in HA are shown in FIG. 4. As mentioned previously, HA is developed for a micro-inhomogeneous media with a periodic micro-structure based on a new type of perturbation theory.

FIG. 5 shows a typical example of a micro-inhomogeneous material, that is, a granite specimen. The nstituent minerals of granite are quartz, feldspar and mica. The interatomic potential models employed are given by Equation (3) and Equation (4), and the parameters for each mineral are found in FIG. 6. Next, by using the statistical thermodynamics procedure, bulk properties of each constituent material are calculated. For example, the stress a (that is, the x-axial stress) is calculated as shown in FIG. 7 corresponding to the strains for each direction (that is, $\epsilon_1$ to $\epsilon_3$ are the axial strains, and $\epsilon_4$ to $\epsilon_6$ are the shear strains) for quartz under the constant-(NPT) ensemble MD and by the subsequent statistical thermodynamics procedure. Note that the quartz is of a trigonal crystal system, so the responses shown in FIG. 7 are completely anisotropic. By using these results, a model of HA is formed as shown in FIG. 8. The micro-structure is specified by microscope observation.

By applying a load 100 MPa at the top of the specimen, its micro-stress distribution is calculated as shown in FIG. 9. Fortunately this case does not involve any out-of-range value given by FIG. 7, so that another MD calculation is not required for this example. And since this material is a natural one, it is not needed to design the micro-structure optimally.

If the invention is applied for a structure made of composite material (FIG. 10) such as a racing car and Space Shuttle (FIG. 11), the present invention thus makes it possible to re-design its micro-structure optimally, for example, by changing the size of fibers.

The foregoing description of the preferred embodiment of the invention has been presented for purposes of illustration and description. It is not intended to be exhaustive or to be limit the invention to the precise forms disclosed, since many modifications or variations thereof are possible in light of the above teaching. All such modifications and variations are within scope of the invention. The embodiments described herein were chosen and described in order best to explain the principles of the invention and its practical application, thereby to enable others skilled in the art to utilize the invention in various embodiments and with various modifications as are suited to the particular use contemplated therefor. It is intended that the scope of the invention be defined by the claims appended hereto, when interpreted in accordance with the full breadth to which they are legally and equitably entitled.

What is claimed is:

1. A computer implemented method for analyzing behavior of an engineering structure including a micro-inhomogeneous material whose micro- structure includes plural constituent materials and for optimal design of said micro-structure by using a unified procedure for modifying material properties of said constituent materials and thereby modifying global characteristics of said structure, by combining a molecular simulation method with a homogenization analysis, comprising the steps of:

(a) using a molecular simulation method for obtaining molecular-level particle-data which substantially include positions, velocities and/or accelerations of molecules of said constituent materials of said micro-inhomogeneous material under a set of material limit conditions;

(b) applying a statistical thermodynamic procedure to said molecular level particle-data for determining volume-averaged inhomogeneous material properties, defined as bulk properties of said constituent materials and of interfaces that substantially comprise boundaries of said plural constituent materials;

(c) applying a homogenization analysis for a set of differential equations in which said bulk properties are used for predicting behavior of said structure, and calculating field variables distributed in said micro-inhomogeneous material;

(d) comparing said field variables in said constituent materials with a predetermined material standard for judging whether or not to accept said material limit conditions for said constituent materials;

(e) if said comparison of step (d) determines that said material limit conditions should not be accepted, changing said material limit conditions, and applying said steps (a) to (d) repeatedly until the comparison of step (d) indicates that said material limit conditions are to be accepted, (f) if said micro-inhomogeneous material is a manufactured material, judging whether or not said microstructure is appropriate in the sense that said field variables are in accordance with a predetermined standard;

(g) when said step (f) is performed and does not give an affirmative answer, changing a geometry and/or a type of at least one of said constituent materials and repeating said steps (a) to (f) until an affirmative answer is obtained in said step (f); and (h) changing a material property of at least one of said constituent materials of said micro-inhomogeneous material in accordance with at least one of said material limit conditions judged acceptable by said step (d) and said geometry and/or shape of said step (g) which are acceptable in accordance with an affirmative determination obtained in said step (f).

2. A computer implemented method according to claim 1, wherein said step (a) of using a molecular simulation method comprises obtaining said particle-data of each of said constituent materials and interfaces of said micro-inhomogeneous material under said material limit conditions.

3. A computer implemented method according to claim 2, wherein said step (b) comprises applying, said statistical thermodynamic procedure to said particle-data for determining bulk properties of each of said constituent materials and interfaces of said micro-inhomogeneous material as functions of said particle-data.

4. A computer implemented method for analyzing behavior of a structure including a micro-inhomogeneous material whose micro-structure includes plural constituent materials and for optimal design of said micro-structure by using a unified procedure combining a molecular simulation method and a homogenization analysis to modify material properties of said constituent materials and thereby to modify global characteristics of said structure, comprising the steps of:

(a) using a molecular simulation method for obtaining molecular-level particle-data substantially including positions, velocities and/or accelerations of molecules of said constituent materials of said micro-inhomogeneous material under predetermined initial boundary conditions;

(b) applying a statistical thermodynamic procedure to said molecular level particle-data for determining volume-averaged inhomogeneous material properties, defined as bulk properties of said constituent materials and of interfaces that substantially comprise boundaries of said constituent materials;

(c) applying a homogenization analysis for a set of differential equations in which said bulk properties are used for predicting behavior of said structure, and calculating field variables distributed in said micro-inhomogeneous material;

(d) comparing said field variables in said constituent materials with a predetermined value for judging whether or not to accept said predetermined initial boundary conditions for said constituent materials;

(e) if said comparison of step (d) determines not to accept said predetermined initial boundary conditions, changing said predetermined initial boundary conditions, and applying said steps (a) to (d) repeatedly until an affirmative answer is obtained in said step (d);

(f) if said micro-inhomogeneous material is an artificial product, judging whether or not said micro-structure is appropriate by comparing said field variables with a predetermined standard;

(g) if said comparison of step (f) determines that said field variables do not meet said predetermined standard, changing a geometry and/or a type of at least one of said constituent materials and repeating said steps (a) to (f) until said step (f) determines that said field variables meet said predetermined standard; and (h) providing a material property for said constituent materials of said micro-inhomogeneous material in accordance with said initial boundary conditions acceptable in said step (d) and said geometry and/or type acceptable in said step (f).

5. A computer implemented method according to claim 4, wherein said step (a) of using a molecular simulation method comprises obtaining said molecular level particle-data of each of said constituent materials and interfaces of said micro-inhomogeneous material under said predetermined initial boundary conditions.

6. A computer implemented method according to claim 5, wherein said step (b) comprises applying said statistical thermodynamic procedure to said molecular level particle-data for determining bulk properties of each of said constituent materials and interfaces of said micro-inhomogeneous material as functions of said particle-data.

7. A computer implemented method according to claim 4, wherein said step of calculating field variables comprises calculating stress and strain distributed in said micro-inhomogeneous material.

8. A computer implemented method according to claim 4, wherein said step of providing a material property for said constituent materials comprises providing a shape for at least one constituent material of a micro-structure of a micro-inhomogeneous material.

9. A computer implemented method according to claim 8, wherein:

said initial boundary conditions are obtained from a shape of at least one constituent material, and said step (e) of changing said predetermined initial boundary conditions comprises changing said shape of said at least one constituent material, thereby modifying at least said one constituent material and said structure including a micro-inhomogeneous material.

10. A computer implemented method according to claim 4, wherein said step of providing a material property for said constituent materials comprises changing interface conditions of constituent materials of said micro-structure of said micro-inhomogeneous material.

11. A computer implemented method according to claim 10, wherein:

said initial boundary conditions are obtained from interface conditions of at least one constituent material, and said step (e) of changing said predetermined initial boundary conditions comprises changing said interface conditions of said at least one constituent material, thereby modifying a material property of at least said one constituent material and said global characteristics of said structure including said micro-inhomogeneous material.

12. A computer implemented method according to claim 4, wherein said step of using a molecular simulation method comprises using a molecular dynamics method.

13. A computer implemented method according to claim 4, wherein said step of using a molecular simulation method comprises using a Monte Carlo method.

14. A computer implemented method according to claim 4, wherein said step of using a molecular simulation method comprises using a molecular mechanics method.

15. A computer implemented method according to claim 4, wherein said step of applying a statistical thermodynamic procedure comprises the further step of obtaining stochastic properties for each constituent material of said micro-inhomogeneous material by applying a molecular dynamics method to each said constituent material.

16. A computer implemented method according to claim 1, wherein:

said molecular simulation method specifics physico-chemical characteristics of each constituent material as required material properties thereof;

said step of applying a homogenization analysis comprises introducing said material properties specified by said molecular simulation method into said homogenization analysis, said step of calculating said field variables comprises calculating variables including at least one of displacement, temperature and stress;

said step (d) comprises determining whether or not a failure will occur in said structure as a result of said comparing; and said step (e) comprises changing at least one of said material and said structure if said step (d) determines that a failure will occur.

* * * * *